United States Patent [19]
Baker

[11] Patent Number: 5,679,514
[45] Date of Patent: Oct. 21, 1997

[54] METHOD FOR DETERMINING THE SEX OF BIRDS

[75] Inventor: Robert James Baker, Lubbock, Tex.

[73] Assignee: Texas Tech University, Lubbock, Tex.

[21] Appl. No.: 250,638

[22] Filed: May 27, 1994

Related U.S. Application Data

[63] Continuation of Ser. No. 999,229, Dec. 31, 1992, abandoned.

[51] Int. Cl.⁶ ................................................. C12Q 1/68
[52] U.S. Cl. ........................... 435/6; 536/24.3; 536/24.31
[58] Field of Search ............................ 435/6; 536/24.31, 536/24.3

[56] References Cited

U.S. PATENT DOCUMENTS 4,987,066  1/1991  Epplen ......................................... 435/6

OTHER PUBLICATIONS

Saitoh et al., Chromosoma (1989) 98: 250–258.

*Primary Examiner*—Scott W. Houtteman
*Attorney, Agent, or Firm*—Ansel M. Schwartz

[57] ABSTRACT

The present invention pertains to a method for determining nucleotides of a bird's W specific chromosome. The method comprises the steps of (a) obtaining a DNA sequence which includes the W specific chromosome from the bird. Then, there is the step of identifying nucleotides of the DNA sequence of the W specific chromosome. The present invention also pertains to a method of determining a sex of a bird, and a method of determining genetic relatedness between two birds. The present invention also pertains to a method for identifying a bird. Moreover, the present invention pertains to a method for determining predictive pairing for the genetic diversity of two birds. In another embodiment, the present invention pertains to a method for determining reproductive competence of a bird. In yet another embodiment, the present invention pertains to a method for predicting reproductive output of two or more birds. The present invention also pertains to a method for determining nucleotides of a bird's W specific chromosome. The method comprises the step of obtaining biological material of the bird. Then, there is the step of introducing a desired microsatellite probe to the biological material so that the W specific chromosome is indicated.

22 Claims, 2 Drawing Sheets

METHOD FOR DETERMINING THE SEX OF BIRDS

This is a continuation of application Ser. No. 07/999,229 filed on Dec. 31, 1992, now abandoned.

FIELD OF THE INVENTION

The present invention is related to diagnosing birds. More specifically, the present invention is related to identifying aspects of the DNA of a bird to identify it, its sex, its relationship with respect to other birds, and predictive of reproductive competence and reproductive output.

BACKGROUND OF THE INVENTION

Many species of birds, being sexually monomorphic, do not display phenotypic differences between the sexes especially in immature individuals. This is true for some commercial species (i.e., parrots and ratites), and for certain endangered species, such as the California Condor (*Gynnogyps californianus*), and Whooping Crane (*Grus americana*). Other non-endangered species, such as the Canada Goose (*Branta Canadensis*), do not manifest sex-specific phenotypes.

Gender determinations can be performed in sexually monomorphic birds through surgical examination. However, this procedure is less practical when dealing with expensive or endangered species because it is invasive and places the individuals being tested at risk. Alternatively, sex identification can sometimes be made through karyotype analysis. However, karyotyping may be unreliable due to difficulties in obtaining avian chromosome spreads, lack of distinguishable sex chromosomes, or both (Prus, S. E., and S. M. Schmutz. 1987. Comparative efficiency and accuracy of surgical and cytogenetic sexing in psitticines. Avian Diseases 31:420–424).

The inability to identify gender in a reliable and non-invasive manner in some birds represents an impediment to captive propagation programs, whether such programs are designed for commercial or restoration purposes. Of value would be the development of DNA-based gender tests for birds. Because the red blood cells of birds contain nuclei, only a small volume of blood (10–100 ul) is required to provide sufficient DNA for multiple tests (Longmire, J. L., A. K. Lewis, N. C. Brown, J. M. Buckingham, L. M. Clark, M. D. Jones, L. J. Meincke, J. M. Meyne, R. L. Ratliff, F. A. Ray, R. P. Wagner, and R. K. Moyzis. 1988. Isolation and molecular characterization of a highly polymorphic centromeric tandem repeat in the family Falconidae Genomics 2:14–24). Such volumes of blood can be drawn easily and safely by venipuncture, or collected from a simple nail-clipping procedure. In addition, many endangered arian species are already the subjects of DNA fingerprinting studies to determine levels of genetic diversity and relatedness within natural and captive populations (Brock, M. K. and B. N. White. 1991. Multifragment alleles in DNA fingerprints of the Parrot, *Amazona ventralis*. J. of Heredity 82: 209–212; Longmire, J. L., G. F. Gee, C. L. Hardekopf, and G. A. Mark. Establishing paternity in whooping cranes (*Grus americana*) by DNA fingerprint analysis. The Auk, in press; Geyer, C. J., O. A. Ryder, L. G. Chennick, and E. A. Thompson. 1992. Analysis of relatedness in California condors from DNA fingerprints. Submitted to Mol. Biol. Evol; Maltbie, M. 1992. DNA fingerprints as a measure of genetic similarity in the endangered species, Attwater's Prairie-Chicken. M. S. Thesis, Texas Tech University). Thus, it would be helpful to identify DNA sequence probes that enable sex identification in the same analyses that generate highly polymorphic patterns achieved in DNA fingerprinting.

Microsatellites consisting of simple repeating nucleotide sequences found ubiquitously in the genomes of higher organisms might be used to achieve this goal. Simple repeats are commonly used to generate DNA fingerprints (Epplen, J. T., H. Ammer, C. Epplen, C. Kammerbauer, R. Mitreiter, L. Roewer, W. Schwaiger, V. Steimle, H. Zischler, E. Albert, A. Andreas, B. Beyermann, W. Meyer, J. Buitkamp, I. Nanda, M. Schmid, P. Nurnberg, S. D. J. Pena, H. Poche, W. Sprecher, M. Schartl, K. Weising, and A. Yassouridis. 1991. Oligonucleotide fingerprinting using simple repeat motifs: A convenient, ubiquitously applicable method to detect hypervariability for multiple purposes. In; DNA fingerprinting: Approaches and applications (T. Burke, G. Dolf, A. Jeffreys, and R. Wolff, Eds). Birkhauser Press, Basil), and certain microsatellites have been previously shown to be sex-linked in some species. Kashi, Y., F. Iraqi, Y. Tikochinski, B. Ruzitski, A. Nave, J. S. Beckmann, A. Freidmann, M. Soller and Y. Gruenbaum. (1990). (TG)n uncovers sex-specific hybridization pattern in cattle. Genomics 7:31–36 reported that the dinucleotide repeat $(TG)_n$ revealed sex-specific restriction patterns in cattle. The tetranucleotide repeat $(GACA)_4$ was found to provide sex identification in certain reptiles (Epplen, J. T., H. Ammer, C. Epplen, C. Kammerbauer, R. Mitreiter, L. Roewer, W. Schwaiger, V. Steimle, H. Zischler, E. Albert, A. Andreas, B. Beyermann, W. Meyer, J. Buitkamp, I. Nanda, M. Schmid, P. Nurnberg, S. D. J. Pena, H. Poche, W. Sprecher, M. Schartl, K. Weising, and A. Yassouridis. 1991. Oligonucleotide fingerprinting using simple repeat motifs: A convenient, ubiquitously applicable method to detect hypervariability for multiple purposes. In; DNA fingerprinting: Approaches and applications (T. Burke, G. Dolf, A. Jeffreys, and R. Wolff, Eds). Birkhauser Press, Basil). In birds, the M13 minisatellite detected female-specific restriction patterns in Mauritious Kestrels (*Falco punctatus*) and Peregrine Falcons (*Falco peregrinus*) (Longmire, J. L., R. E. Ambrose, N. C. Brown, T. J. Cade, T. L. Maechtle, W. S. Seegar, F. P. Ward and C. M. White. 1991. Use of sex-linked minisatellite fragments to investigate genetic differentiation and migration of North American populations of the peregrine falcon (*Falcon peregrinus*). Pages 217–229. In; DNA fingerprinting: Approaches and applications (T. Burke, G. Dolf, A. Jeffreys, and R. Wolff, Eds). Birkhauser Press, Basil), and the trinucleotide repeat $(CTT)_n$ has been shown to be sex-linked in pigeons and in chickens (Epplen, J. T., H. Ammer, C. Epplen, C. Kammerbauer, R. Mitreiter, L. Roewer, W. Schwaiger, V. Steimle, H. Zischler, E. Albert, A. Andreas, B. Beyermann, W. Meyer, J. Buitkamp, I. Nanda, M. Schmid, P. Nurnberg, S. D. J. Pena, H. Poche, W. Sprecher, M. Schartl, K. Weising, and A. Yassouridis. 1991. Oligonucleotide fingerprinting using simple repeat motifs: A convenient, ubiquitously applicable method to detect hypervariability for multiple purposes. In; DNA fingerprinting: Approaches and applications (T. Burke, G. Dolf, A. Jeffreys, and R. Wolff, Eds). Birkhauser Press, Basil).

The present invention is directed to the use of sexing probes preferably based on microsatellite repeats.

SUMMARY OF THE INVENTION

The present invention pertains to a method for determining nucleotides of a bird's W specific chromosome. The method comprises the steps of (a) obtaining a DNA sequence which is present on the W specific chromosome from the bird. Then, there is the step of identifying nucleotides of the DNA sequence of the W specific chromosome.

The present invention also pertains to a method of determining a sex of a bird, and a method of determining genetic relatedness between two birds. The present invention also pertains to a method for identifying a bird. Moreover, the present invention pertains to a method for determining predictive pairing for the genetic diversity of two birds. In another embodiment, the present invention pertains to a method for determining reproductive competence of a bird. In yet another embodiment, the present invention pertains to a method for predicting reproductive output of two or more birds associated with problems of inbreeding depression.

The present invention also pertains to a method for determining nucleotides of a bird's W specific chromosome. The method comprises the step of obtaining biological material of the bird. Then, there is the step of introducing a desired microsatellite probe to the biological material so that the W specific chromosome is indicated.

BRIEF DESCRIPTION OF THE DRAWINGS

In the accompanying drawings, the preferred embodiment of the invention and preferred methods of practicing the invention are illustrated in which:

FIG. 1a is of Hinfl digested Canada Goose DNAs hybridized to $(CT)_n$. FIG. 1b is of Peregrine Falcon (P.F.) and California Condor (C.C.) DNAs digested with HaeIII and hybridized to $(CT)_n$. FIG. 1c is of HaeIII digested Peregrine Falcon DNAs hybridized to $(GT)_n$. In each panel, males designated M, and females designated F. Size standards ( ) included undigested, and HindIII digested bacteriophage lambda DNA, and HaeIII digested 0X174 DNA. Female-specific fragments indicated in each panel by dashes at approximately 50 kb.

DESCRIPTION OF THE PREFERRED EMBODIMENT

Figure 1A:
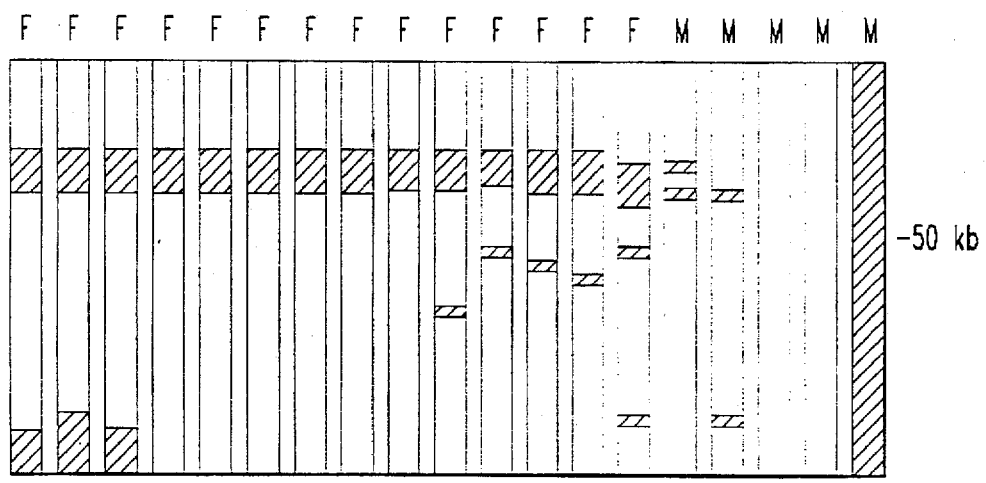
FIGS. 1a-1c are representative blots showing sex-specific DNA hybridization patterns. Of each DNA, 10 ug was digested with excess restriction enzyme and electrophoresed within 0.8% agarose gels. Resulting southern blots were hybridized to microsatellite probes.

The present invention pertains to a method for determining nucleotides of a bird's W specific chromosome. The method comprises the steps of (a) obtaining a DNA sequence which is present on the W specific chromosome from the bird. There is also the step of (b) identifying nucleotides of the DNA sequence of the W specific chromosome.

The step (b) of identifying nucleotides can include the steps of (c) separating fragments of the DNA sequence by size. Then, there is the step of (d) tagging the fragments of the DNA sequence of interest. Next, there is the step of (e) displaying the tagged fragments so the diagnostic specific nucleotide sequences can be identified.

The step (c) of separating fragments can include the step (f) of separating electrophoretically fragments of the DNA sequence by size. The step (d) of tagging the fragments can include the step (g) of hybridizing the fragments of DNA sequence. Furthermore, the step (e) of displaying the tagged fragments can include the step (h) of taking a picture, preferably an x-ray picture of the DNA sequence such that the desired fragments appear as bands on the x-ray picture. Preferably, the step (g) of hybridizing the fragments includes the step (i) of introducing desired microsatellite probes to the fragments of the DNA sequence.

After the step (h) of taking an x-ray picture, there can be the step (j) of determining the bird is female if an intense band corresponding to a molecular weight of about 50 kilobases is present in the x-ray picture.

Alternatively, before the step (h) of taking an x-ray picture, there can be the step (k) of repeating steps (a)-(g) and (i) for other birds. In this embodiment, the step (h) includes the step (l) of taking the x-ray picture so bands associated with all the birds are included in it. Preferably, after the step (l) of taking the x-ray picture, there is the step (m) of scoring all readable bands and determining their frequency among a given bird taxon.

After the step (l) of taking the x-ray picture, there is the step (m) of scoring all readable bands and determining an amount of bandsharing in a pairwise comparison of the birds.

Moreover, the step (a) of obtaining a DNA sequence can include the step (m) of collecting biological material of the bird having DNA. The step (m) of collecting biological material can include the step (n) of obtaining a cell from the biological material. Then, there can be included the step (o) of separating DNA from the cell. Additionally, there can be the step (p) of applying restriction enzyme to the DNA to separate the DNA sequence from the DNA.

The present invention also pertains to a method for determining the sex of a bird. The method comprises the steps of obtaining biological material of the bird. Then, there is the step of identifying the sex of the bird from the biological material. Preferably, the biological material includes a desired DNA sequence which is present on the W specific chromosome. The step of obtaining biological material of the bird can be the obtaining step which is described above. The step of identifying the sex of the bird and the biological material can also be the associated identifying step described above and specifically the step (j) of determining if the bird is female.

Additionally, the present invention pertains to a method for determining genetic relatedness between two birds. The method comprises the steps of obtaining a DNA sequence from each bird. This step of obtaining a DNA sequence from each bird can preferably be the same as the obtaining step described above with respect to a single bird. Then, there is the step of separating fragments of each DNA sequence by size. The step of separating fragments can preferably be the same as the separating step described above. Then, there is the step of comparing the fragments of each DNA sequence to identify whether they are substantially in common. This latter step uses the percentage of shared fragments. Closely related birds (brothers, sisters, offspring) share a greater number of bands than distantly related birds. For instance, if 40% or greater of fragments are shared, the birds are substantially in common. Typically, the percentage of shared fragments is determined on a case by case basis. First, for example, known brothers and sisters can be reviewed for a general percentage of shared fragments. Then, known birds of the subject bird taxon which are unrelated can be reviewed to determine a percentage of shared bands for unrelated birds relative to shared bands of the related birds. From this information, a standard can be established which can be used as a basis for comparison for subsequently analyzed unknown birds of that taxon.

Moreover, the present invention also pertains to a method for identifying a bird. The method comprises the steps of obtaining a DNA sequence from the bird. Preferably, the obtaining step can be the same as the obtaining step described above. Then, there is the step of separating fragments of the DNA sequence by size. Preferably, the step of separating fragments can be the same as the separating step described above. Then, there is the step of hybridizing the fragments with desired microsatellite probes. Next, there is the step of recording locations of the fragments. At some later time, the recorded locations can be reviewed with subsequently recorded locations obtained by the above steps to determine if the bird is the same bird as identified earlier. In samples from the same individual, all bands will be shared.

The present invention pertains to a method for determining predictive pairing for genetic diversity of two birds. The method comprises the steps of obtaining a DNA sequence from each bird. The obtaining step can be the same as the obtaining step described above. Then, there is the step of separating fragments of each DNA sequence by size. The separating step can be the same separating step that is described above. Then, there is the step of hybridizing the fragments with desired microsatellite probes. Next, there is the step of comparing the fragments of each DNA sequence to identify whether they are substantially dissimilar. For each taxon, the number of bands present is identified and through determination of the frequency of each band in the population, the relatedness of any two individuals can be predicted. Essentially, the determination of dissimilarity is the same as described above for commonality, but the focus is now on how unrelated are two birds.

Moreover, the present invention pertains to a method for determining reproductive competence of a bird. The method comprises the steps of obtaining a DNA sequence which includes a W specific chromosome from the bird. The obtaining step can be the same obtaining step as described above. Then, there is the step of hybridizing the DNA sequence with desired microsatellite probes to label, preferably the fragment from, the W specific chromosome. Next, there is the step of taking a picture of the label associated with the W specific chromosome. The picture taking step can be the same picture taking step as described above. Next, there is the step of measuring intensity of the label. Then, there is the step of comparing intensity of the label against intensity of labels of a W specific chromosome of reproductively competent males and females. For instance, a table of intensities can be created with known sexed birds and used as a basis for comparison of a corresponding label for a given bird. For purposes herein, competence refers to either male or female distinctiveness, or lack thereof (intersexed-sexually mixed birds which can be expected to have limited reproductive capability).

The present invention pertains to a method for predicting reproductive output of two or more birds. Reproductive output, for purposes herein, is understood to refer to the number of eggs a mating pair produces, the fertility of the eggs the mating pair produces, and the survivorship of the eggs and subsequent offspring of the mating pair. The method comprises the steps of obtaining a DNA sequence from each bird. The obtaining step can be the same obtaining step as described above. Then, there is the step of separating fragments of each DNA sequence by size. The separating step can be the same separating step as described above. Next, there is the step of hybridizing the fragments with desired microsatellite probes. Then, there is the step of comparing the fragments of each DNA sequence to known DNA fragments, preferably in a table, with respect to reproductive output to maximize production of offspring. For instance, mated pairs of birds which have been studied over time with respect to the number of eggs, fertility and the survivorship thereof can be used to create a table of known DNA fragments with respect to the bird's reproductive output. This table of fragments will then reflect the known reproductive output of mated pairs of birds.

In the operation of the preferred embodiment, the obtaining step preferably includes the following steps.

1) Source of DNA

About 0.25–0.50 ml of freshly collected blood, macerated pieces of tissues (½ to ⅓ grams), or any other tissue that contains nucleated cells can be used as a source of DNA. This includes blood left inside egg shells that remains from a newly hatched chick.

2) Lysis of Cell Membranes

The tissue is placed in 5 ml of lysis buffer (0.1M Tris-HCl pH 8.0, 0.1M ethylenediamine-tetraacetic acid (EDTA), 0.01M NaCl, 0.5% (w/v) sodium dodecyl sulfate (SDS)) contained in sterile 15 ml polypropylene tubes and shaken. This frees the DNA from inside the cell and permits it to be in solution in the buffer. Proteinase K (10 mg/ml) is added at this time to the buffer if tissue other than blood is used. Samples can be stored in lysis buffer at room temperature for long periods of time.

3) Destruction of Proteins

To remove proteins from the solution containing the DNA, proteinase K (10 mg/ml) is added to 0.5 mg per ml, and the samples are incubated at 37° C. on a tube rotator (slow rotation) overnight.

4) Extraction of DNA

An equal volume of phenol (molecular grade, preheated to ⁻50° C.) saturated in 1× TE buffer (100× TE make 484.4 grams of Tris, 152 grams of EDTA and bring up to volume of 4 liters with distilled water) is added to each sample (after overnight incubation with proteinase K). The phenol/DNA buffer solution is placed on a rotator at room temperature for 30 minutes. This is followed by centrifugation for 5 minutes at 2000 rpm.

The top layer (aqueous layer) is removed from the centrifuge tube and placed in dialysis tubing (molecular weight cut off 12,000–14,000) and the samples are then dialyzed in 1× TE at 4° C. against 3–4 changes of 1× TE or longer until the smell of phenol can no longer be detected.

5) Cleaning Up of Samples

A) If samples did not appear clear at this step, they are put through steps 3–4 again until samples appear clean.

B) The undigested samples of DNA from an individual must be greater than 50 kb in size if the sex identification is possible so this next step is to determine the molecular weight and the purity of DNA samples so no false male samples will be identified. Therefore, undigested samples of DNA are electrophoresed on an agarose gel and compared to a 40 kb size marker.

The step of identifying nucleotides of the DNA sequence preferably includes the following steps.

6) Preparation of Gel for Electrophorese

An 8% agarose gel is prepared (350 ml of 1× TAE buffer (49.3 Trizma base, 4.1 grams EDTA, 9.1 ml of Acetic acid, and fill to 1 liter pH to 8.2 if needed) and 2.8 grams of agarose, boil for 3 minutes, allow to cool to about 60° with stirring, and then pour into 20 cm×25 cm gel box with an appropriate comb to produce 20 wells that will hold approximately 42 µl of DNA solution and allow to set for one hour).

A 10 µl alloquot of each sample is added to 2 µl of 6× bluecrose and pipitted into a well.

Samples are loaded into the 8% agarose gel, usually with 2 to 3 markers (100 ng uncut lambda DNA and 500 ng Hind III cut lambda DNA) placed in some of the wells.

7) Electrophoreses of DNA Samples

The gel is run at 40 volts in 1× TAE buffer for about 3 hours. This is done to visualize the DNA samples. DNA samples can be visualized with an ultra-violet light source and photographed with polaroid film (Polaroid instant film, type 57, 3000 speed). High molecular weight DNA (over 40 to 50 kilobases) that appears clean of RNA is ready to go to the next step. If samples have a significant amount of RNA (which is common if tissues other than blood are used), they are put through a RNA purification step. RNA appears as small sized fragments on the gel.

8) RNA Purification Step

A 1/10 volume of RNase (1 mg/ml) is added to the sample and put in 37° C. incubator for 2 to 3 hours, then a half volume of 10% SDS is added to stop the reaction. Step 4 of phenol extraction, described above, is repeated.

9) Preparation of DNA in Known Quantities (300 μg/ml)

Clean, high molecular weight DNA Is quantified by UV spectroscopy (Maniatus et al., 1982, incorporated by reference). Dilution of samples for spectroscopy is 25 μl of sample plus 475 μl of 1× TE. The $A^{260}$ reading is multiplied by 1000 to give the concentration of the DNA samples in μg/ml. Samples are adjusted to 300 μg/ml by precipitating out the DNA by adding 0.1 sample volume of 3M sodium acetate and 2.5–3 times sample volume cold (0° C.) 200 proof ethanol. The concentration of the DNA samples multiplied by its original volume after dialysis is then divided by 300 to indicate the amount of 1× TE that is needed to be added to get final concentration of 300 μg/ml. After 1× TE is added, samples are put on rotator overnight at 4° C. and then stored at 4° C. when not in use.

10) Digestions of DNA with Restriction Enzymes

A digestion is set up for each sample: 33 μl or 10 micrograms of DNA sample, 4 μl of 10× restriction enzyme buffer (Promega buffer B), and 3 μl of restriction enzyme (Promega HinfI). Digestions are well mixed and tough agitated before being placed in 37° C. incubator overnight.

Enzyme digestion is stopped through heat killing. Digestions are placed in 70° C. for 10 minutes.

11) Gel Electrophoreses for Southern Analysis

An 8% agarose gel is prepared (350 ml of 1× TAE and 2.8 grams of agarose, boil for 3 minutes, allow to cool to ~60° with stirring, pour into 20 cm×25 cm gel box and allow to set for 1 hour), then submerge in 1× TAE buffer in gel rig.

Four microliters of 6× bluecross is mixed with each digested sample.

Two to three wells are filled with 20 μl of mixed marker plus 2 μl of 6× bluecross.

Gels usually have 20 wells, 17 wells for samples and 3 wells for markers. Markers are set up so they are asymmetrical. The location of samples can then be easily assessed and the order of samples has minimal probability of being confused.

A 41 μl of sample of a given bird is loaded into a well. A total of 17 birds can be run (loaded) on a single gel with 3 wells reserved for molecular weight markers. A 21 μl sample of marker is loaded into each of the 3 marker wells.

The gel is run at 40 volts for about 36 to 48 hours.

After completion of a run, a polaroid photograph using ultraviolet light is taken with a red filter to document the extent of digestion and that movement through gel is normal.

12) Southern Transfer

A) Gels are submerged for 5 minutes in 0.25M HCl, followed by two 15-minute submersions in 0.4M NaOH (fresh NaOH each submersion). A stir bar is placed in the middle of the gel box for each submersion to keep liquid moving.

B) Restriction fragments are transferred to a nylon membrane (Boehringer Mannheim) using the procedure of Southern (1975), incorporated by reference.

C) Transfers are allowed to take place overnight and then taken apart. Membranes are washed gently by hand in 2× SSC, followed by one 15 minute wash in a neutralization solution (0.5M Tris pH 7.5, 1.5M NaCl). This is followed by two 15-minute washes in 2×SSC. All these washes are done at room temperature on an orbital mixer. Membranes are dried between two clean sheets of Whatman paper (3 MM chromatography paper) and stored in plastic covering until used.

13) Hybridization

Preparation of the Southern Transfer Membrane

A) Immediately prior to hybridization, membranes are washed in 0.1×SSC, 0.1% SDS at 60° C. for 1 hour on an orbital mixer.

B) Membranes are then treated with a prehybridization solution at 42° C. for 45 minutes to 1 hour on an orbital mixer. Prehybridization mixture for 1 to 2 membranes in a sealed bag is made of a total of a 100 ml of the following ingredients: 30 ml 20× SSC, 35 ml formamide, 1 ml 0.5M EDTA, 5 ml 20% SDS, 0.25 grams of powdered milk, and brought up to volume of 100 ml with distilled water. For more than 2 membranes, they are put in a tub (usually Tubberware) with enough prehybridization solution so that membranes are submerged. Prehybridation solution is stirred and warmed until clear before it was put on membranes.

Nick Translation of the DNA Probe

DNA probes are labeled with $^{32}$P as follows: 1.0 μg probe DNA (in this procedure it is poly (dA-dG)·(dC-dT) supplied by Pharmacia), 5 μl of marker, 1 μl each of cold dATP, dGTP, and dTTp, 5 μl $^{32}$P dCTP, 5 μl of 10× nick translation buffer (0.5M TrisCl (pH 7.5), 0.1M MgSO$_4$, 1 mM dithiothreitol, 5 μg/ml bovine serum albumin), 5 μl DNase/Polymerase I, and distilled water is added to make 50 μl total). This solution is incubated for 45 minutes at 15° C. Solutions of 50 μl 1× TE and 10 μl 0.5% SDS are then added to the probe and then run through a G-50 in 1× TE sephadex spin column by centrifugation. After this, the labeled probe is treated with 1/9 volume of 1M NaOH and then incubates for 10 minutes at 37° C. The probe is added directly to the prehybridization solution containing the membranes and allowed to hybridize overnight at 42° C. on an orbital mixer. A kit for labeling a probe is sold by Clontech Laboratories, Inc. of Palo Alto, Calif. which has full instructions therein to accomplish the same, incorporated by reference. (Note, a BT buffer is comprised of 8.4 grams of sodium bicarbonate, 17.53 grams of sodium chloride and 0.5 ml Tween 20 (Sigma Co.). Alternatively, the trinucleotide repeat (CTT)$_n$ was labeled with [$^{32}$P]dCTP using the primer extension method described by Feinberg, A. P., and B. Vogelstein. 1983. A technique for radiolabeling DNA restriction fragments to high specific activities. Anal. Biochem. 132:6–13), incorporated by reference.

Following overnight hybridization, membranes are rinsed in 2× SSC at room temperature followed by a 15-minute wash in 2× SSC on an orbital mixer at room temperature. Membranes are then washed twice for 15 minutes each in 1× SSC, 0.1% SDS at 50° C. on an orbital mixer. Membranes are blotted dry with a clean sheets of Whatman paper and wrapped in saran wrap without wrinkles.

Exposure of Film with the Radioactive Probe

The membranes are then placed in a cassette with intensifying screens and a piece of film (Kodak XAR-5) and exposed overnight at −70° C. If after overnight exposure, the film is inadequately exposed a second piece of film is exposed for a longer time frame. The length of exposure is varied until the desired level of exposure is obtained.

Scoring of Autoradiograms (See DNA fingerprints as a measure of genetic similarity in the endangered species, Attwater's Prairie-Chicken. M. S. Thesis, Texas Tech University, incorporated by reference)

There are two ways to score autoradiograms. One method is to just score polymorphic fragments and to calculate their frequency among a bird taxon. The polymorphic fragment frequency is calculated as the total number of individuals with a specific band (not shared among all individuals) divided by the total number of individuals. This frequency is the average of all polymorphic bands scored on the autoradiogram and could then be compared to other frequencies for different species of birds in work done by other investigators using DNA fingerprinting (Burke and Bruford, 1987; Longmire et al., 1992, incorporated by reference). The second approach is to score all readable bands even if they are shared among all individuals. This allows calculation of an index of similarity among all individuals in a pairwise comparison using the same DNA fingerprinting probe and digested with the same enzyme. The formula used to calculate the amount of band sharing in a pairwise comparison is the total number of bands shared by two birds in the comparison divided by their total number of bands (Wetton et al., 1987, incorporated by reference). This will allow the investigator to see which bird is more varied from the other birds in the comparison using that specific enzyme/probe combination. To keep consistency in scoring, standard markers are run at both ends and the middle of the gel, and sometimes samples from individual birds are duplicated at opposite ends of the gel so that the chance of error could be reduced.

DNA Marker

For many birds, the microsatellite probe, $(TC)_n$, is the probe that is able to identify the sex marker of an individual. The sex marker is a very intense band of high molecular weight estimated to be about 50 kilobases in female birds.

Figure 1B:
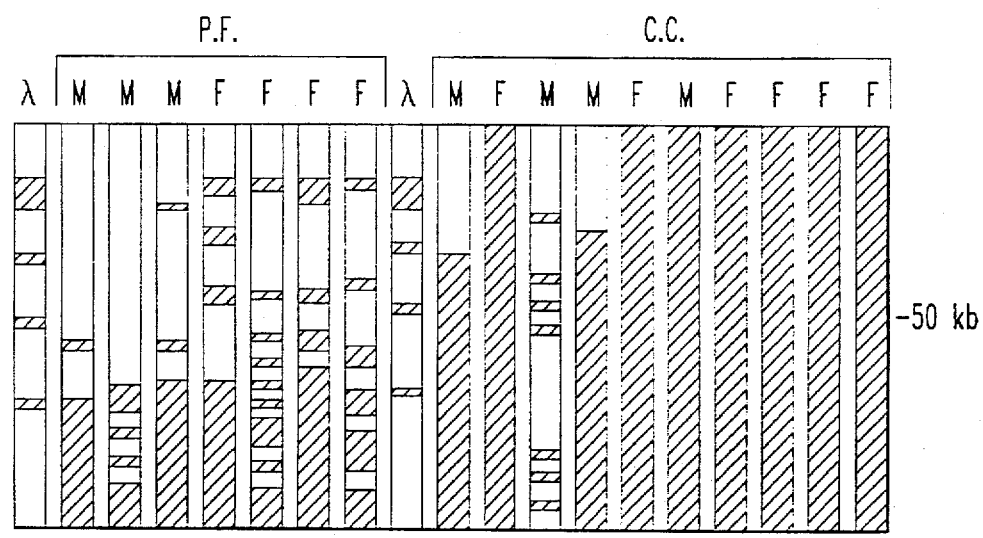
Figure 1C:
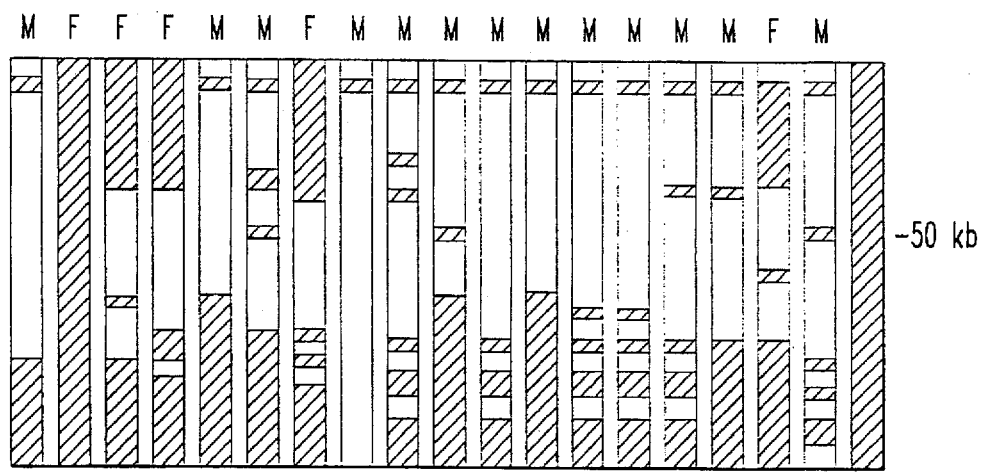

Results include the observation of high molecular weight, female-specific restriction fragments at approximately 50 kilobase pairs (kb) in the majority of species that were tested following digestion with certain restriction enzymes and hybridization to various microsatellite probes (Table 1, FIG. 1). The 50 kb fragment has been shown to be present on the W specific chromosome in the California condor (see FIG. 2) and its presence on the W specific chromosome is the basis for gender identification.

TABLE 1

Sex identification in birds using various microsatellite probes. Numbers indicate restriction enzymes successfully used to reveal high molecular weight, female-specific, microsatellite fragments (1 = HaeIII; 2 = HinfI; 3 = PstI). Zero (0) indicates female-specific microsatellite fragments not detected. Asterisks indicate reduced hybridization signal intensity. ND-not done.

| Species | Microsatellite Probe | | | |
| --- | --- | --- | --- | --- |
| | $(CT)_n$ | $(GT)_n$ | $(CG)_n$ | $(CTT)_n$ |
| Peregrine Falcon (9 F, 16 M) | 1 | 1 | 0* | 0* |
| California Condor (6 F, 3 M) | 1,2 | 0 | 0* | 0 |
| Canada Goose (14 F, 5 M) | 2 | 0 | 0* | 2 |
| House Sparrow (5 F, 5 M) | 0 | 0 | 0* | 0 |
| Wild Turkey (7 F, 4 M) | 1,3 | 0 | 0* | ND |

TABLE 1-continued

Sex identification in birds using various microsatellite probes. Numbers indicate restriction enzymes successfully used to reveal high molecular weight, female-specific, microsatellite fragments (1 = HaeIII; 2 = HinfI; 3 = PstI). Zero (0) indicates female-specific microsatellite fragments not detected. Asterisks indicate reduced hybridization signal intensity. ND-not done.

| Species | Microsatellite Probe | | | |
| --- | --- | --- | --- | --- |
| | $(CT)_n$ | $(GT)_n$ | $(CG)_n$ | $(CTT)_n$ |
| Attwater Prairie-Chicken (2 F, 14 M) | 1 | 0 | 0* | 1 |
| Greater Prairie-Chicken (9 F, 6 M) | 1,2 | 0 | 0* | 1,2 |
| Chattering Lory (2 F, 2 M) | 0 | ND | 0* | 0 |
| Whooping Crane (5 F, 5 M) | 0 | 0 | 0* | 0* |

Dinucleotide repeat $(CT)_n$ revealed sex-specific fragments in HaeIII digested Peregrine Falcon DNA; California Condor DNA digested with HaeIII or HinfI; Canada Goose DNA digested with HinfI; Wild Turkey (*Meleagris gallopazo*) DNA digested with HaeIII or PstI; Attwater's Prairie-Chicken (*Tympanuchus cupido attwateri*) DNA digested with HinfI or HaeIII. Dinucleotide repeat $(GT)_n$ revealed female-specific HaeIII restriction fragments in the Peregrine. Trinucleotide repeat $(CTT)_n$ hybridized to female-specific HinfI restriction fragments in the Canada Goose and Attwater's Prairie Chicken DNA after digestion with HaeIII, and in Greater Prairie-Chicken DNA following digestion with HaeIII or HinfI. In the above cases, sex determination by DNA analysis matched exactly to morphometric examination. All of the microsatellite probes hybridized to DNAs sufficiently to allow overnight autoradiographic exposures, except $(CTT)_n$ which showed reduced hybridization to DNA from the Peregrine and Whooping Crane, and $(CG)_n$ which produced little or no detectable hybridization to any DNA sample. In addition, each of the microsatellite probes, except $(CG)_n$, revealed highly polymorphic (DNA fingerprint) patterns in all species that were tested.

Of interest were the variable results obtained depending upon which microsatellite probes were used with the different species. Among the birds that displayed female-specific patterns in response to at least one repeat probe, certain probes revealed sex-specific patterns in some species but not in others. For example, $(CTT)_n$ revealed sex-specific patterns in the Canada Goose and Prairie-Chickens, but not in the Peregrine or California Condor. On the other hand, only the Peregrine displayed sex-specific patterns following hybridization to $(GT)_n$. Only $(CG)_n$ was non-informative in all species. The observation that $(CG)_n$ did not hybridize to these avian DNAs is not surprising considering that CG is the rarest dinucleotide within vertebrate genomes, and probably does not exist as a moderate copy-number repeat (Stallings, R. L. 1992. CpG suppression in vertebrate genomes does not account for the rarity of (CpG)n microsatellite repeats. Genomics 17:890–891; Sved, J., and A, Bird. 1990. The expected equilibrium of the CpG dinucleotide in vertebrate genomes under a mutational model. Proc. Natl. Acad. Sci. USA 87:4692–4696).

The set of microsatellite probes tested allowed unambiguous gender testing in the Peregrine Falcon, California Condor, Wild Turkey, Canada Goose, Greater Prairie-Chicken, and Attwater's Prairie-Chicken. Taking into account that there are only 4 nucleotides present in DNA, circular permutation of repeat sequences, as well as strand complementarity, there are 6 dinucleotide, 12 trinucleotide, 39 tetranucleotide, 109 pentanucleotide, and 366 possible hexanucleotide repeat probes. These probes can be produced using an Oligo nucleotide synthesizing machine or obtained from any of a variety of professional companies which provide customized synthesis of DNA.

The procedure for discovering microsatellite probes that will work, for, as yet, untested species would consist of the following steps: by taking into account the circular permutations of repeat sequences, as well as strand complementarity of DNA, there are 6 dinucleotides, 12 trinucleotides, 39 tetranucleotides, 109 pentanucleotides, and 366 possible hexanucleotide repeat probes. There is a high probability that all permutations will not be required as certain combinations are rarely found in the genome as tandem repeats; for example, GT and CT are more common in the genome than are GC and AT. After the relative frequency of microsatellites is assessed for a sample of bird species (e.g., Table 1 in Longmire et al., ms), then a bank of probes can be developed to maximize the probability of gender identification in a more universal manner and thereby reduce experimental procedures to identify the putative species-specific probe. The larger the data base, the less time will be required to discover the correct probe for previously uninvestigated species.

In the instance of species in which one of the four dinucleotides failed to resolve gender of individuals, the nature (sequence) of the microsatellite that resolves gender can be identified by digestion of nuclear DNA samples with a combination of 4-base-cutter restriction enzymes. The large molecular sized product on an agarose gel can be isolated and cloned and sequenced to identify the microsatellite(s) associated with the sex chromosomes.

The present invention also pertains to a method for determining nucleotides of a bird's W specific chromosome. The method comprises the step of obtaining biological material of the bird. Then, there is the step of introducing a desired microsatellite probe to the biological material so that the W specific chromosome is indicated. Preferably, the biological material includes nucleated blood and the introducing step includes the step of hybridizing in situ the blood with the desired microsatellite probe. The in situ hybridizing step is described in Moyzis, R. K., L. Albright, M. F. Bartholdi, L. S. Cram, L. L. Deaven, C. E. Hildebrand, N. E. Josta, J. L. Longmire, J. Meyne, and T. S. Robinson. 1987. Human chromosome-specific repetitive DNA sequences: Novel markers for genetic analysis. Chromosoma 95:375–386; Moyzis, R. K., J. M. Buckingham, L. S. Cram, L. L. Deaven, M. D. Jones, J. Meyne, R. L. Ratliff, and J. R. Wu. 1988. A highly conserved repetitive DNA sequence $(TTAGGG)_n$, present at the telomeres of human chromosomes. Proc. Nat. Acad. Sci. USA 85:6622–6626, incorporated by reference.

Figure 2:
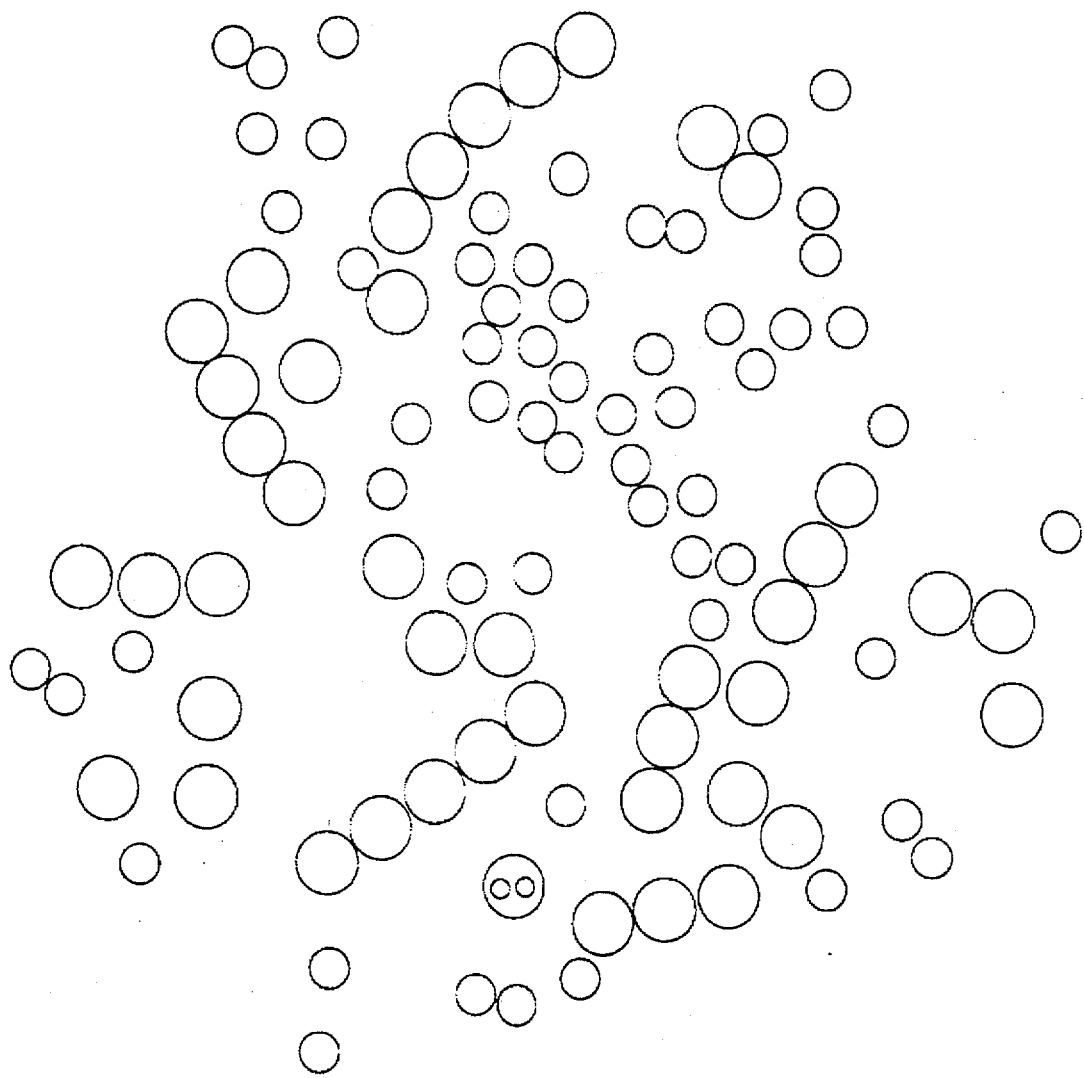
FIG. 2 is a photograph of chromosomes of a female individual of the California condor.

FIG. 2 is a photograph of chromosomes of a female individual of the California condor showing the presence of the W specific chromosome identified by two yellow dots. The gross morphology of the W specific chromosome has been identified by karyotyping by Dr. Oliver Ryder of the San Diego Zoo and the chromosome identified by yellow matches the description of the W specific chromosome described by Ryder. In males of the California condor, no such element is present. Note also that in the interphase nucleus at the corner of the photo, the yellow indicating the presence of the W specific chromosome can be seen. This means that in this embodiment, biological material, and preferably interphase blood cells, can be used to sex condors without any DNA isolation. Once the proper microsatellite has been identified for the W specific chromosome of any bird taxon, this method can be applied to identifying the gender of individual birds of that taxon.

A system for any of the above methods (identification, sex, relationship with other birds, reproductive capability, etc.) can include the desired microsatellite probes, a container for biological material, materials necessary to prepare the biological material for tagging with the probes, and a mechanism to identify the presence of the probes, all of which are consistent with the described methods above.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for determining the size of a specific nucleotide segment of either a Peregrine Falcon's, California Condor's, Canadian Goose's, Wild Turkey's, Attwater Prairie-Chicken's or a Greater Prairie-Chicken's W specific chromosome comprising the steps of:
   (a) obtaining a DNA sequence which is present on the W specific chromosome from the bird;
   (aa) introducing microsatellite probes to the DNA sequence so they interact, said microsatellite probes being either dinucleotide, trinucleotide, tetranucleotide, pentanucleotide or hexanucleotide repeat probes; and
   (b) identifying nucleotides of the DNA sequence of the W specific chromosome from the probes which have interacted with the DNA sequence so nucleotides of the bird's W specific chromosome are determined.

2. A method as described in claim 1 wherein step (b) includes the steps of (c) separating fragments of the DNA sequence by size, (d) tagging the fragments of the DNA sequence of interest, and (e) displaying the tagged fragments so nucleotides can be identified.

3. A method as described in claim 2 wherein step (c) includes the step (f) of separating electrophoretically fragments of the DNA sequence by size; the step (d) includes the step (g) of hybridizing the fragments of DNA sequence, and the step (e) includes the step (h) of taking an x-ray picture of the DNA sequence such that the fragments appear as bands on the x-ray picture.

4. A method as described in claim 3 wherein step (g) includes the step (i) of introducing microsatellite probes to the fragments of the DNA sequence.

5. A method as described in claim 4 including after step (h), the step (i) of determining the bird is female if a band corresponding to a molecular weight of about 50 kilobases is present the in x-ray picture.

6. A method as described in claim 4 including before the step (h), there is the step (k) of repeating steps (a)–(g) and (i) for other birds, wherein the step (h) includes the step (l) of taking the x-ray picture so bands associated with all the birds are included in it.

7. A method as described in claim 6 including after the step (l), there is the step (m) of scoring all readable bands and determining their frequency among a given bird taxon.

8. A method as described in claim 6 including after the step (l), there is the step (n) of scoring all readable bands and determining an amount of band sharing in a pairwise comparison of individual birds.

9. A method as described in claim 8 wherein step (a) includes the step (m) of collecting biological material of the bird having DNA.

10. A method as described in claim 9 wherein the step (m) includes the step (n) of obtaining a cell from the biological material, the step (o) of separating DNA from the cell, and the step (p) of applying restriction enzyme to the DNA to separate the DNA sequence from the DNA.

11. A method for determining genetic relatedness between two birds of either a Peregrine Falcon, California Condor, Canadian Goose, Wild Turkey, Attwater Prairie-Chicken or a Greater Prairie-Chicken comprising the steps of:

obtaining a DNA sequence which is present on a W specific chromosome from each bird;

separating fragments of each DNA sequence by size;

hybridizing the fragments with microsatellite probes, said microsatellite probes being either dinucleotide, trinucleotide, tetranucleotide, pentanucleotide or hexanucleotide repeat probes; and comparing the fragments of each DNA sequence to identify whether they are substantially in common so the genetic relatedness between the two birds is determined.

12. A method for identifying either a Peregrine Falcon, California Condor, Canadian Goose, Wild Turkey, Attwater Prairie-Chicken or a Greater Prairie-Chicken comprising the steps of:

obtaining a DNA sequence which is present on a W specific chromosome from the bird;

separating fragments of the DNA sequence by size;

hybridizing the fragments with microsatellite probes, said microsatellite probes being either dinucleotide, trinucleotide, tetranucleotide, pentanucleotide or hexanucleotide repeat probes; and recording locations of the fragments so the bird is identified.

13. A method for determining predictive pairing for genetic diversity of two birds Of either a Peregrine Falcon, California Condor, Canadian Goose, Wild Turkey, Attwater Prairie-Chicken or a Greater Prairie-Chicken comprising the steps of:

obtaining a DNA sequence which is present on a W specific chromosome from each bird;

separating fragments of each DNA sequence by size;

hybridizing the fragments with desired microsatellite probes, said microsatellite probes being either dinucleotide, trinucleotide, tetranucleotide, pentanucleotide or hexanucleotide repeat probes; and comparing the fragments of each DNA sequence to identify whether they are substantially dissimilar so predictive pairing for genetic diversity is determined.

14. A method for determining reproductive competence of a bird comprising the steps of:

obtaining a DNA sequence which includes a W specific chromosome from the bird;

hybridizing the DNA sequence with microsatellite probes to label the W specific chromosome;

taking a picture of the label associated with the W specific chromosome;

measuring intensity of the label; and comparing intensity of the label against intensity of labels of W specific chromosome of reproductively competent males and females.

15. A method for determining reproductive output of two or more birds of either a Peregrine Falcon, California Condor, Canadian Goose, Wild Turkey, Attwater Prairie-Chicken or a Greater Prairie-Chicken comprising the steps of:

obtaining a DNA sequence which is present on a W specific chromosome from each bird;

separating fragments of each DNA sequence by size;

hybridizing the fragments with microsatellite probes, said microsatellite probes being either dinucleotide, trinucleotide, tetranucleotide, pentanucleotide or hexanucleotide repeat probes; and comparing the fragments of each DNA sequence to known DNA fragments with respect to reproductive output to predict production of offspring so reproductive output of the two birds is determined.

16. A method for determining the size of a specific nucleotide segment of either a Peregrine Falcon's, California Condor's, Canadian Goose's, Wild Turkey's, Attwater Prairie-Chicken's or a Greater Prairie-Chicken's W specific chromosome comprising the steps of:

obtaining nucleated blood of the bird; and hybridizing in situ the blood with a microsatellite probe so nucleotides of the bird's W specific chromosome are determined.

17. A method as described in claim 1 including after step (aa), there is the step of (g) digesting the DNA sequence with a combination of 4-base-cutter restriction enzymes if the microsatellite probes do not reveal the gender of the bird.

18. A method for determining the sex of either a Peregrine Falcon, California Condor, Canadian Goose, Wild Turkey, Attwater Prairie-Chicken or a Greater Prairie-Chicken from the respective bird's w-specific chromosome comprising the steps of:

obtaining a DNA sequence which is present on the W specific chromosome from the bird;

introducing microsatellite probes to the DNA sequence so they interact to reveal the sex of the bird, said microsatellite probes being either dinucleotide, trinucleotide, tetranucleotide, pentanucleotide or hexanucleotide repeat probes; and identifying the sex of the bird from the probes which have interacted with the DNA sequence.

19. A method as described in claim 18 including after the introducing step, there is the step of digesting the DNA sequence with a combination of 4-base-cutter restriction enzymes if the microsatellite probes do not reveal the sex of the bird.

20. A method for determining the sex of either a Peregrine Falcon, California Condor, Canadian Goose, Wild Turkey, Attwater Prairie-Chicken or a Greater Prairie-Chicken comprising the steps of:

obtaining nucleated blood of the bird;

hybridizing in situ the blood with a microsatellite probe; and identifying the sex of the bird from the hybridized blood.

21. A method as described in claim 10 wherein the probe is either (CT)n, (GT)n, (CG)n or (CTT)n.

22. A method for determining which microsatellite probe will reveal the sex of either a Peregrine Falcon, California Condor, Canadian Goose, Wild Turkey, Attwater Prairie-Chicken or a Greater Prairie-Chicken from the respective bird's W chromosome comprising the steps of:

introducing dinucleotide, trinucleotide, tetranucleotide, pentanucleotide and hexanucleotide repeat microsatellite probes to a DNA sequence having a W specific chromosome of the bird;

assessing the relative frequency of each microsatellite probe that has labeled the DNA sequence; and forming a database identifying probability that a given microsatellite will reveal a bird's sex, said probability corresponding to the relative frequency of the given microsatellite labeling the DNA sequence, so the database will identify which microsatellites can be used for a bird to determine the bird's sex.

* * * * *